United States Patent [19] [11] 4,172,815

Jacobs [45] Oct. 30, 1979

[54] SIMULTANEOUS PRODUCTION OF JET FUEL AND DIESEL FUEL

[75] Inventor: William L. Jacobs, Crystal Lake, Ill.

[73] Assignee: UOP Inc., Des Plaines, Ill.

[21] Appl. No.: 944,503

[22] Filed: Sep. 21, 1978

[51] Int. Cl.$^2$ .......................... C10G 13/02; C07C 5/24; C10L 1/04

[52] U.S. Cl. ...................................... 208/111; 208/102

[58] Field of Search ........................... 208/15, 111, 102

[56] References Cited

U.S. PATENT DOCUMENTS

| | | | |
|---|---|---|---|
| 3,245,901 | 4/1966 | Beuther et al. | 208/110 |
| 3,540,999 | 11/1970 | Jacobs | 208/15 X |
| 3,799,864 | 3/1974 | Bunn et al. | 208/80 |

*Primary Examiner*—Delbert E. Gantz
*Assistant Examiner*—G. E. Schmitkons
*Attorney, Agent, or Firm*—James R. Hoatson, Jr.; John G. Cutts, Jr.; William H. Page, II

[57] ABSTRACT

A single stage hydrocracking process for the simultaneous production of jet fuel and diesel fuel.

6 Claims, 1 Drawing Figure

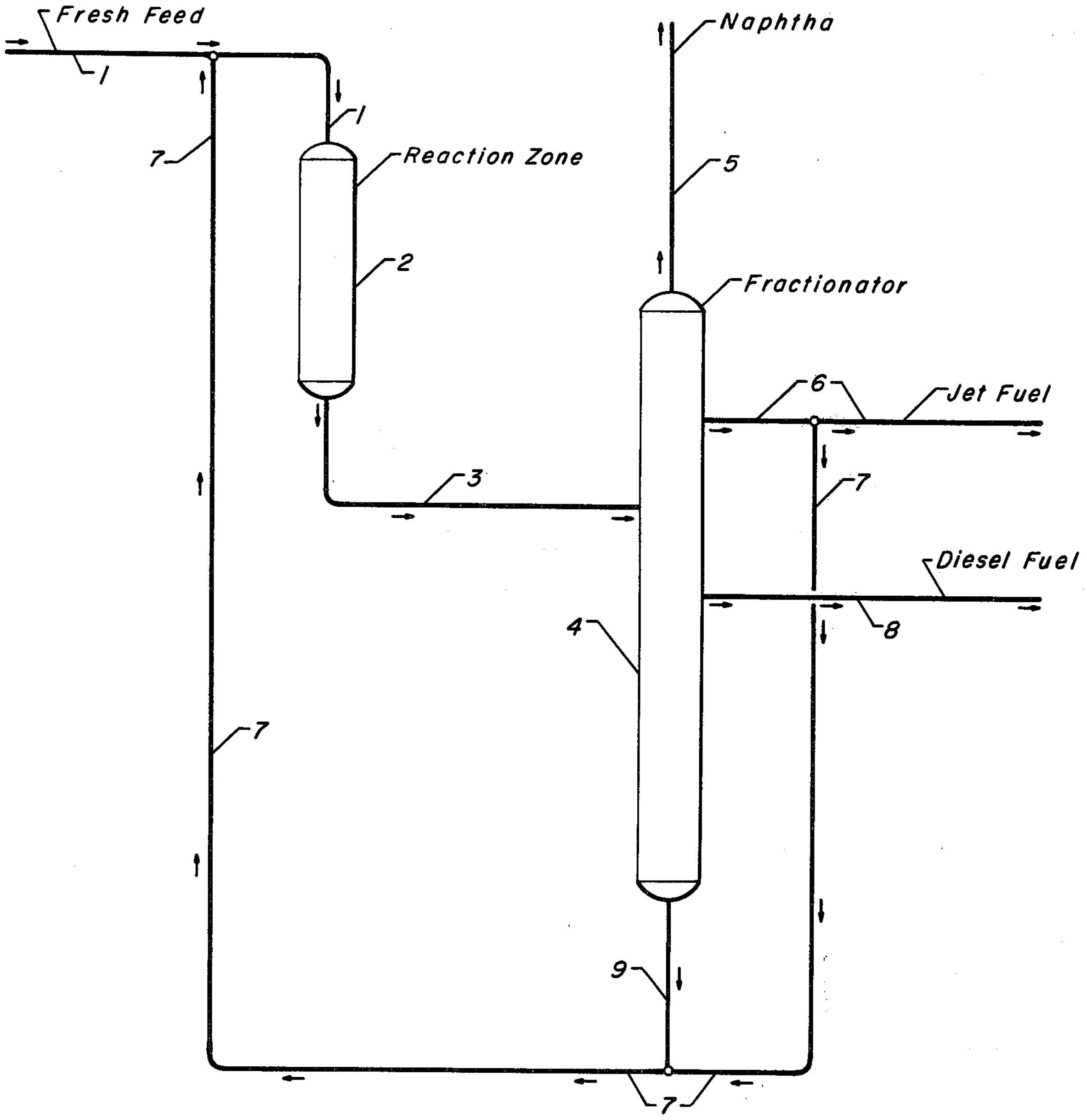
Fresh Feed
1
1
7
Reaction Zone
2
Naphtha
5
Fractionator
6
Jet Fuel
7
3
Diesel Fuel
4
8
7
9
7

SIMULTANEOUS PRODUCTION OF JET FUEL AND DIESEL FUEL

BACKGROUND OF THE INVENTION

The present invention is directed toward a single stage hydrocracking process for the simultaneous production of jet fuel and diesel fuel. Suitable feed stocks include vacuum gas oils, atmospheric gas oils and any other hydrocarbon charge stocks boiling at a temperature greater than about 500° F. Hydrocracking, also commonly referred to as "destructive hydrogenation", is distinguished from the simple addition of hydrogen to unsaturated bonds between carbon atoms, since it effects definite changes in the molecular structure of the hydrocarbons being processed. Hydrocracking may, therefore, be designated as cracking under hydrogenation conditions such that the lower-boiling products of the cracking reactions are substantially more saturated than when hydrogen, or material supplying hydrogen, is not present. Although some hydrocracking processes are conducted thermally, the preferred processing technique involves the utilization of a catalytic composite possessing a high degree of hydrocracking activity. In virtually all hydrocracking processes, whether thermal or catalytic, controlled or selective cracking is desirable from the standpoint of producing an increased yield of liquid product having improved, advantageous physical and/or chemical characteristics.

Selective hydrocracking is especially important when processing hydrocarbons and mixtures of hydrocarbons which boil at temperatures above the gasoline and/or the middle-distillate boiling range; that is, hydrocarbons and mixtures of hydrocarbons, as well as the various hydrocarbon fractions and distillates, having a boiling range indicating an initial boiling point of from about 600° F. to 700° F., and an end boiling point as high as 1000° F. or more. Selective hydrocracking of such hydrocarbon fractions results in greater yield of hydrocarbons boiling within and below the middle-distillate boiling range. Selective hydrocracking involves the splitting of a higher-boiling hydrocarbon molecule into two molecules, both of which are normally liquid hydrocarbons.

A major disadvantage of nonselective or uncontrolled hydrocracking, is the more rapid formation of increased quantities of coke and other heavy carbonaceous material which becomes deposited upon the catalyst and decreases, or destroys, the activity thereof to catalyze the desired reactions. Such deactivation results in a shorter acceptable processing cycle or period, with the inherent necessity for more frequent regeneration of the catalyst, or total replacement thereof with fresh catalyst.

The utilization of the process of the present invention permits milder reaction conditions to be employed in the catalytic reaction zone which facilitates the maximization of selectivity during hydrocracking and the minimization of coke formation on the catalyst.

PRIOR ART

Candor compels acknowledgment of the fact that a considerable amount of published literature, including patents, exist in the general area of hydrocracking hydrocarbon charge stocks including descriptions of catalysts, catalyst preparation, process operating conditions and flow schemes.

No appreciation of the simultaneous production of jet fuel and diesel fuel via hydrocracking with attendant recycle of at least a portion of the hydrocracking reaction zone effluent boiling in the kerosene range has been evident.

OBJECTS AND EMBODIMENTS

The primary object of the present invention is to provide a process for the simultaneous production of jet fuel and diesel fuel from a hydrocarbon charge stock having an initial boiling point greater than about 500° F. and containing a substantial proportion of cyclic hydrocarbons which comprises the steps of: (a) reacting said charge stock with hydrogen in a catalytic reaction zone at a maximum catalyst bed temperature below about 900° F. and a pressure greater than about 1000 psig.; (b) separating the reaction zone product effluent into a jet fuel boiling range stream and a diesel fuel boiling range stream; and (c) recycling at least a portion of said jet fuel boiling range stream to said catalytic reaction zone.

Another object of my invention is to provide a process for converting heavier hydrocarbonaceous material into jet fuel kerosene fractions, accompanied by maximum production of diesel fuel.

Another object is to produce jet fuel kerosene fractions meeting smoke point, aromatic concentration and sulfur content requirements.

SUMMARY OF THE INVENTION

As hereinbefore set forth, the primary purpose of my invention is to provide a process which affords the simultaneous production of jet fuel and diesel fuel.

Detailed requirements for various jet fuels may be found in the ASTM Specifications for Aviation Turbine Fuels. Of these requirements, the three most critical are considered to be the smoke point, generally not less than 25 mm, the concentration of aromatic hydrocarbons, generally less than about 20 volume percent and the concentration of sulfur.

In the event a feed stock is processed under milder operating conditions to yield the desired product mix, the smoke point of the kerosene or jet fuel product may be 3–5 mm below the maximum smoke point thereby producing off-spec jet fuel product. During the simultaneous production of diesel fuel and jet fuel, it appears that the aromatic hydrocarbons in the higher boiling (in this case, diesel fuel) are preferentially hydrogenated. This results in an increase in the aromatic hydrocarbon content of the kerosene with a corresponding decrease in its smoke point.

While neither the precise composition, nor the method of manufacturing the various catalytic composites is considered essential to my invention, a catalyst capable of efficiently hydrocracking heavy hydrocarbonaceous oil is preferred. Suitable catalytic composites comprise metallic components selected from the metals of the Group VI-B and VIII of the Periodic Table, and compounds thereof. Thus, in accordance with the Periodic Table of the Elements, E. H. Sargent & Co., 1964, suitable metallic components are those selected from the group consisting of chromium, molybdenum, tungsten, iron, ruthenium, osmium, cobalt, rhodium, iridium, nickel, palladium and platinum. It is further preferred that the components of the catalyst possess the propensity for effecting hydrocracking while simultaneously producing a substantially sulfur-free normally liquid hydrocarbon product with selectivity towards a combination of jet fuel and diesel fuel.

Suitable catalytic composites generally comprise from about 1 to about 40 weight percent of a Group VI-B metallic component and from about 0.1 to about 10 weight percent of a Group VIII metallic component. It is understood that these concentrations, as well as those hereinafter set forth, are computed on the basis of the elemental metals, regardless of the precise state in which they exist within the catalytic composite. These catalytically active metallic components are generally composited with a suitable siliceous refractory inorganic oxide carrier material, the quantity of silica determining the degree of hydrocracking activity. Suitable refractory inorganic oxides include zeolites, silica, alumina, zirconia, magnesia, titania, thoria, boria, hafnia, etc. and mixtures thereof.

In practicing the present invention, the charge is admixed with hydrogen in an amount of about 1000 to about 20,000 standard cubic feet per barrel (SCFB). The hydrocarbon and hydrogen mixture is heated to a temperature level such that the catalyst bed temperature is controlled within the range of about 600° F. to a maximum of about 900° F. The catalyst bed inlet temperature is regulated to control the outlet temperature below the maximum level of about 900° F. Since the principal reactions are exothermic in nature, a temperature rise will be experienced as the charge stock passes through the catalyst bed. The reaction zone is maintained under an imposed pressure of from about 1000 to about 4000 psig. and the liquid hourly space velocity (defined as volumes of liquid hydrocarbon charge per hour per volume of catalyst) is in the range of from about 0.1 to about 10.

The product effluent from the reaction zone is separated into a jet fuel fraction, a diesel fuel fraction and a heavy recycle fraction boiling above the diesel fuel boiling range. The heavy recycle fraction together with at least a portion of the jet fuel fraction is returned to the catalytic reaction. The resulting diesel fuel fraction and jet fuel fraction are recovered as finished products. Separation of the reaction zone effluent stream may be performed in any facile manner which may include fractionation.

DESCRIPTION OF THE DRAWING

The process encompassed by my invention is more clearly understood by reference to the accompanying drawing which illustrates one embodiment thereof. In the drawing, only those vessels and process lines required for an understanding of the embodiments have been included. Miscellaneous appurtenances, including valves, controls, instruments, pumps, compressors, heat exchangers, start-up lines, ancillary separation vessels and heat-recovery circuits have either been reduced in number or completely eliminated. The use of this conventional hardware is well within the purview of those skilled in the techniques of petroleum refining processing. It is further understood that the drawing is presented for the sole purpose of illustration, and is not intended to be limited to the particular charge stock, quantities, rates, operation conditions, product yields and/or distribution employed by way of illustration. With reference now to the drawing, the feed stock, for example, a heavy vacuum gas oil is introduced into the process via line 1. The charge stock continues through line 1, being admixed with a hydrocarbon recycle stream which will be subsequently described and is carried via line 7. The hydrocarbon mixture is contacted with a catalytic composite in reaction zone 2 at conditions which include an inlet temperature of about 740° F., a liquid hourly space velocity of 0.6 and a hydrogen circulation rate of 12,000 SCFB. The reaction zone effluent is transported via line 3 into fractionator 4. Fractionator 4 functions at conditions of temperature and pressure which permits the recovery of a naphtha stream via line 5, a jet fuel fraction via line 6, a diesel fuel stream via line 8 and a heavy recycle fraction boiling above the diesel fuel boiling range via line 9. A portion of the jet fuel fraction removed from fractionator 4 via line 6 is recycled via line 7 and line 1 to the catalytic reaction zone as a portion of the hydrocarbon recycle stream mentioned hereinabove. The heavy recycle fraction removed from fractionator 4 via line 9 and is recycled via line 7 and line 1 to the catalytic reaction zone as a portion of the hydrocarbon recycle stream mentioned hereinabove.

EXAMPLE

The following example is herein presented for the purpose of further illustrating the present invention, and to indicate the benefits afforded through the utilization thereof. It is not intended that the present invention be limited unduly by the presentation of this example.

This example is presented to illustrate the results obtained by the prior art processes without kerosene recycle. The charge stock is a gas oil and the pertinent properties of the charge stock are presented in Table I.

TABLE I

| | |
|---|---|
| Gravity, ° API | 22.5 |
| ASTM Distillation, ° F. | |
| IBP | 630 |
| 10 | 730 |
| 30 | 795 |
| 50 | 840 |
| 70 | 890 |
| 90 | 960 |
| EP | 1070 |
| Sulfur, weight percent | 2.50 |
| Nitrogen, p.p.m. | 940 |

It is intended that this gas oil charge stock be converted to the extent of producing about 50—55 volume percent jet fuel and 40—45 volume percent diesel fuel. The operation is effected in a reaction zone system of the type previously described with respect to the embodiment illustrated in the accompanying drawing without kerosene recycle. The catalytic zone is maintained at a pressure of about 2600 psig. and a catalyst bed inlet temperature of 740° F. The liquid hourly space velocity is 0.6 and the hydrogen circulation rate is 12,000 SCFB. The catalyst disposed within the reaction zone is a composite of 2% by weight of Ni and 14% by weight of Mo, computed as the elemental metals, combined with a carrier material of alumina and silica.

At the operating conditions hereinabove described, the gas oil is being converted into 52.7 volume percent jet fuel kerosene having a smoke point of 24 mm and 41.5 volume percent diesel fuel. The jet fuel product does not meet the minimum smoke point specification for commercial consumption.

However, if 50 volume percent of the hydrocarbon boiling in the jet fuel range at these operating conditions is recycled to the catalytic reaction zone, the smoke point of the finished jet fuel boiling range product increases to 27 mm and is then saleable.

The foregoing specification and particularly the example, clearly indicate the method of effecting the present invention and the benefits afforded through the utilization thereof.

I claim as my invention:

1. A process for the simultaneous production of jet fuel and diesel fuel from a hydrocarbon charge stock having an initial boiling point greater than about 500° F. and containing a substantial proportion of cyclic hydrocarbons which comprises the steps of:

(a) reacting said charge stock with hydrogen in a catalytic reaction zone at a maximum catalyst bed temperature below about 900° F. and a pressure greater than about 1000 psig.;

(b) separating the reaction zone product effluent into a jet fuel boiling range stream and a diesel fuel boiling range stream; and, (c) recycling at least a portion of said jet fuel boiling range stream to said catalytic reaction zone.

2. The process of claim 1 wherein said catalytic reaction zone contains a catalyst comprising at least one metallic component from Group VI-B and VIII of the Periodic Table.

3. The process of claim 1 wherein said catalytic reaction zone contains a catalyst comprising a zeolite.

4. The process of claim 1 wherein said catalytic reaction zone contains a catalyst comprising alumina.

5. The process of claim 1 wherein said catalytic reaction zone contains a catalyst comprising silica.

6. The process of claim 1 wherein said catalytic reaction zone contains a catalyst comprising silica and alumina.

* * * * *